(12) United States Patent
Imai et al.

(10) Patent No.: US 11,672,642 B2
(45) Date of Patent: Jun. 13, 2023

(54) FILTER DEVICE

(71) Applicant: TERUMO KABUSHIKI KAISHA, Tokyo (JP)

(72) Inventors: Masaomi Imai, Kofu Yamanashi (JP); Kazuaki Kanamoto, Hadano Kanagawa (JP); Takashi Kitaoka, San Jose, CA (US); Yuki Masubuchi, Cupertino, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/195,606

(22) Filed: Mar. 8, 2021

(65) Prior Publication Data

US 2021/0186674 A1    Jun. 24, 2021

Related U.S. Application Data

(63) Continuation of application No. PCT/JP2019/037029, filed on Sep. 20, 2019.

(30) Foreign Application Priority Data

Sep. 28, 2018   (JP) ............................. JP2018-183440

(51) Int. Cl.
   *A61F 2/01*   (2006.01)
(52) U.S. Cl.
   CPC .......... *A61F 2/0108* (2020.05); *A61F 2/0105* (2020.05); *A61F 2002/016* (2013.01);
   (Continued)

(58) Field of Classification Search
   CPC ............ A61F 2/0108; A61F 2230/0067; A61F 2230/0006; A61F 2002/016; A61F 2/013; A61F 2002/018; A61F 2210/0014; A61F 2230/0076; A61F 2230/008; A61F 2/01; A61F 2230/0093; A61F 2310/00071;
   (Continued)

(56) References Cited

U.S. PATENT DOCUMENTS 9,693,852 B2    7/2017   Lam et al.
10,022,139 B2   7/2018   Kobayashi et al.
(Continued)

FOREIGN PATENT DOCUMENTS

JP      2016-513578 A    5/2016
JP      2017-508552 A    3/2017
(Continued)

OTHER PUBLICATIONS

Extended European Search Report dated Sep. 22, 2021 in corresponding European Patent Application No. 19865963.3, 8 pages.
(Continued)

*Primary Examiner* — Katherine M Shi
(74) *Attorney, Agent, or Firm* — Kim & Stewart LLP

(57) ABSTRACT

A filter device insertable into a biological lumen includes a shaft portion and an elastically deformable portion interlocked with the shaft portion, the deformable portion having a plurality of wires braided in a mesh shape. The wires include wires of a first type, each having a diameter d. A sum of $d^3$ of all of the wires is 0.08 to 0.25 $mm^3$.

19 Claims, 5 Drawing Sheets

(52) U.S. Cl.
CPC ............... *A61F 2210/0014* (2013.01); *A61F 2250/0039* (2013.01)

(58) Field of Classification Search
CPC ..... A61F 2250/0039; A61F 2250/0018; A61B 17/22; A61B 17/221; A61B 2017/2212
See application file for complete search history.

(56) References Cited

U.S. PATENT DOCUMENTS

| | | | |
|---|---|---|---|
| 2002/0091409 A1* | 7/2002 | Sutton | A61F 2/0105 606/200 |
| 2003/0176884 A1* | 9/2003 | Berrada | A61F 2/0105 606/200 |
| 2006/0100662 A1* | 5/2006 | Daniel | A61B 17/221 606/200 |
| 2007/0208373 A1 | 9/2007 | Zaver et al. | |
| 2008/0228028 A1* | 9/2008 | Carlson | D03D 15/283 623/1.13 |
| 2009/0099647 A1* | 4/2009 | Glimsdale | A61B 17/12172 623/1.35 |
| 2015/0272716 A1 | 10/2015 | Pinchuk et al. | |
| 2015/0306311 A1 | 10/2015 | Pinchuk et al. | |
| 2017/0112513 A1 | 4/2017 | Marchand et al. | |
| 2018/0103971 A1 | 4/2018 | Imai et al. | |
| 2018/0193043 A1* | 7/2018 | Marchand | A61F 2/013 |
| 2019/0183519 A1 | 6/2019 | Imai et al. | |

FOREIGN PATENT DOCUMENTS

| | | | |
|---|---|---|---|
| WO | WO-2006012243 A2 * | 2/2006 | ............... A61F 2/01 |
| WO | 2016-067646 A1 | 5/2016 | |
| WO | 2018-043282 A1 | 3/2018 | |

OTHER PUBLICATIONS

English Translation of International Search Report dated Nov. 26, 2019, mailed in counterpart International Application No. PCT/JP2019/037029, 2 page.

English Translation of Written Opinion dated Nov. 26, 2019, mailed in counterpart International Application No. PCT/JP2019/037029, 6 pages.

Notice of Reasons for Refusal dated Mar. 20, 2023, in corresponding Japanese Patent Application No. 2020-549140, 12 pages (with Translation).

* cited by examiner

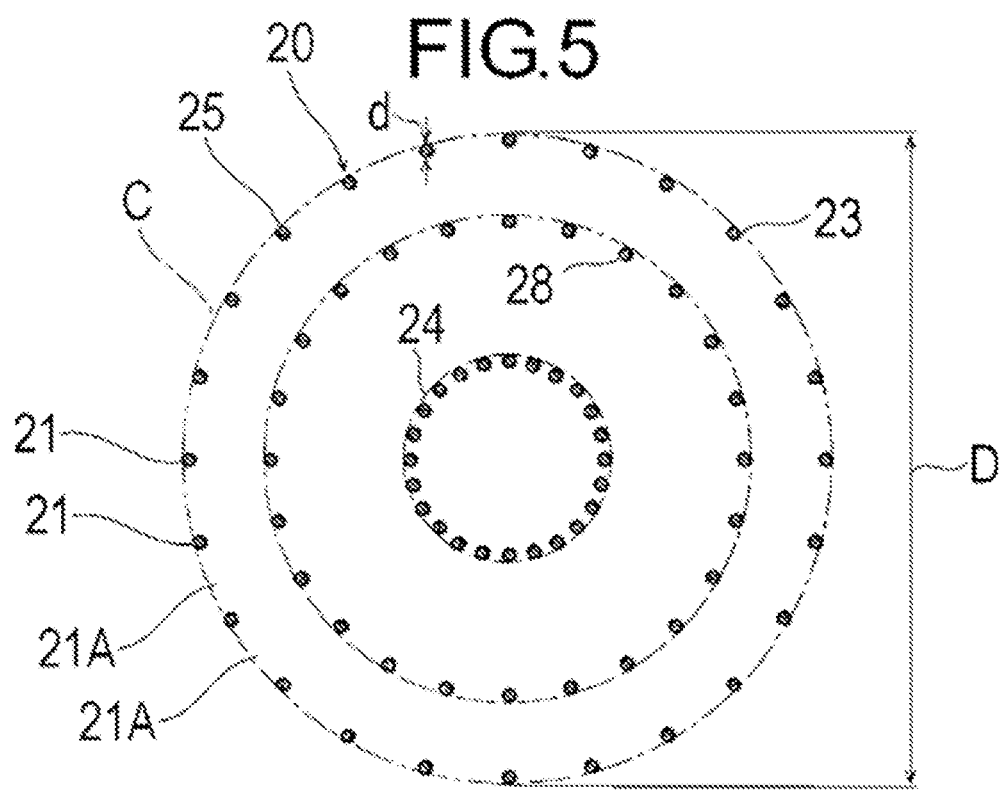

FILTER DEVICE

CROSS-REFERENCE TO RELATED APPLICATION(S)

This application is a continuation of International Patent Application No. PCT/JP2019/037029, filed on Sep. 20, 2019, which is based upon and claims the benefit of priority from Japanese Patent Application No. 2018-183440, filed on Sep. 28, 2018, the entire contents of which are incorporated herein by reference.

BACKGROUND OF THE INVENTION

Field of the Invention

Embodiments described herein generally relate to a filter device inserted into a biological lumen.

Background Art

When a portion of a vein is clogged with a thrombus, the portion may cause pain or may become swollen. In order to treat this condition, there is a method of percutaneously inserting a device to physically break and remove the thrombus. In this treatment, there is a risk of pulmonary embolism when the thrombus completely separated or partially separated from a vascular wall enters a bloodstream and reaches the lung. Therefore, when the treatment is performed, a thrombus solvent is used before and after, and/or during the treatment, or the separated thrombus is aspirated and removed as much as possible during the treatment. However, even when this procedure is performed, there is still a possibility that the separated thrombus having a clinically problematic size may reach the lung.

In order to avoid the pulmonary embolism, a method is known in which a filter for collecting the thrombus flowing inside a blood vessel is indwelled in the blood vessel such as an inferior vena cava. For example, there is a known device in which a filter having a linear body woven in a tubular shape is provided in a distal portion of a wire extending in an elongated manner. The filter can be formed in a cup shape open in a proximal direction by pushing a proximal side portion toward a distal side portion and turning back the filter in an axial direction.

Depending on conditions, there is a possibility that the turned-back filter may have a reduced fixing force to a biological lumen such as the blood vessel. When the fixing force is reduced, the filter is likely to be moved or tilted in a state where the filter indwells the biological lumen. When the filter is moved or tilted, there is a possibility that an object such as the thrombus collected by the filter may be scattered.

SUMMARY OF THE INVENTION

One or more embodiments provide a filter device capable of improving a fixing force to a biological lumen.

A filter device insertable into a biological lumen according to one or more embodiments includes a shaft portion and an elastically deformable portion interlocked with the shaft portion, the deformable portion having a plurality of wires braided in a mesh shape. The wires include wires of a first type, each having a diameter d. A sum of $d^3$ of all of the wires is 0.08 to 0.25 $mm^3$.

In the filter device configured as described above, the expansion portion expanded and caused to indwell the biological lumen receives a stronger force from a biological lumen wall. Therefore, the filter device can have an improved fixing force inside the biological lumen.

BRIEF DESCRIPTION OF THE DRAWINGS

FIG. 5 is a cross-sectional view taken along line A-A in FIG. 3.

DETAILED DESCRIPTION OF THE INVENTION

Figure 1:
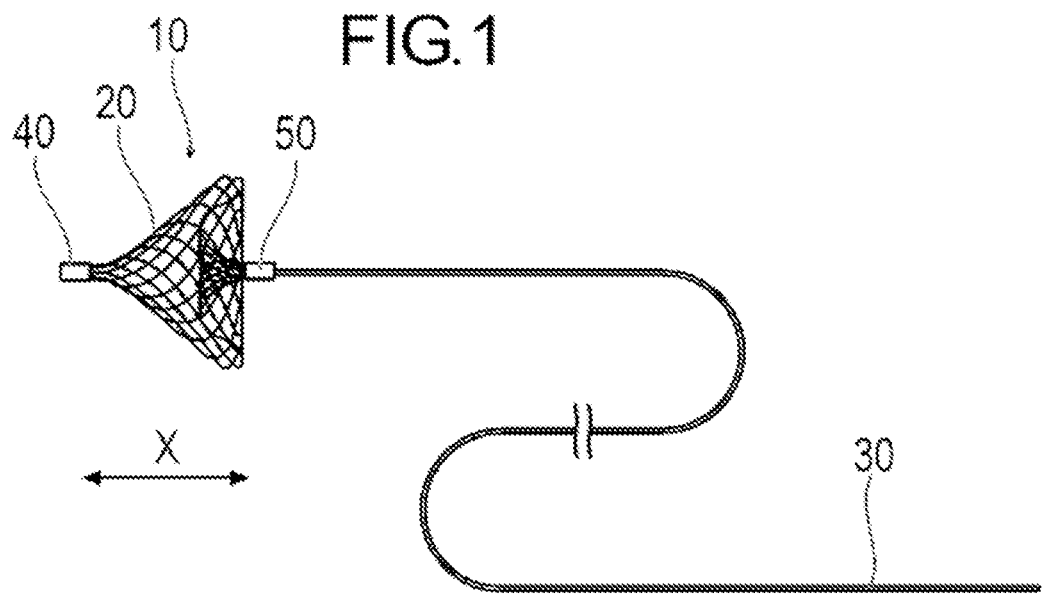
FIG. 1 is a plan view illustrating a filter device according to an embodiment.

Hereinafter, embodiments will be described with reference to the drawings. Dimensional proportions in the drawings may be different from actual proportions.

A filter device 10 according to an embodiment is used to collect an object such as a thrombus, a plaque, and a calcified lesion inside a blood vessel. In the description herein, a side where a device is inserted into the blood vessel will be referred to as a "distal side", and an operating hand-side will be referred to as a "proximal side". A biological lumen into which the filter device 10 is inserted is not limited to the blood vessel, and for example, may be a vessel duct, a ureter, a bile duct, an oviduct, or a hepatic duct. In addition, the object to be collected is not necessarily limited to the thrombus, the plaque or the calcified lesion, and all objects that may exist inside the biological lumen can be collected.

Figure 2:
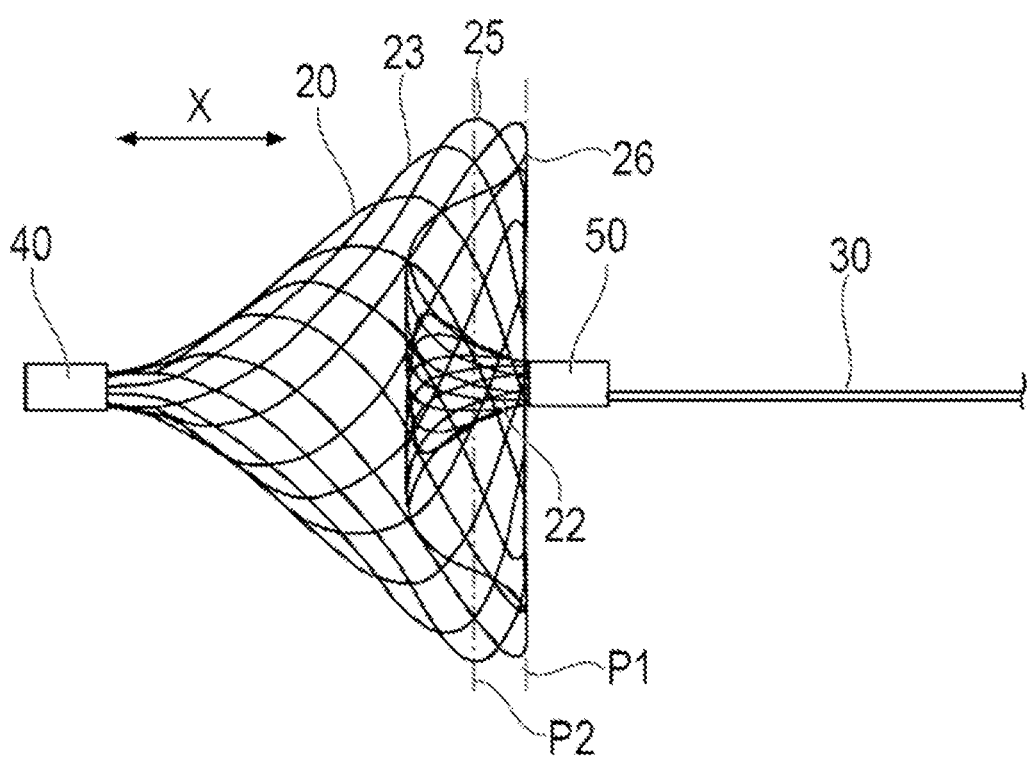
FIG. 2 is a plan view illustrating an expansion portion in a natural state.
Figure 3:
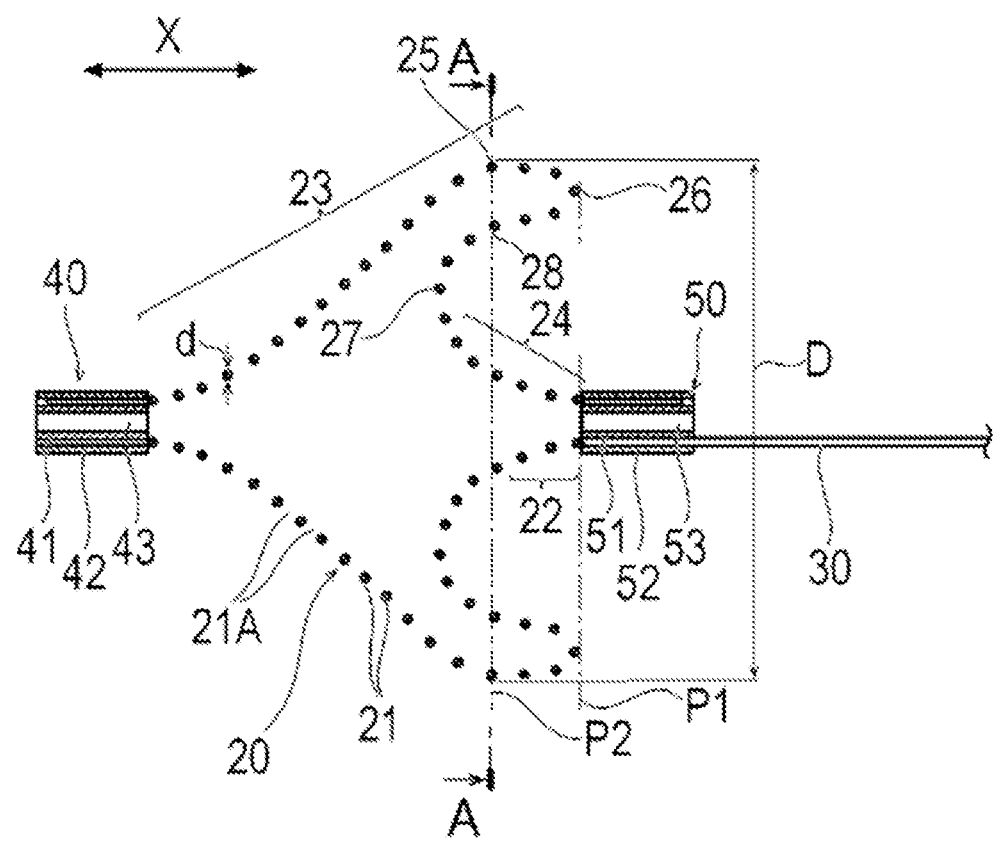
FIG. 3 is a cross-sectional view illustrating the expansion portion in the natural state.

As illustrated in FIGS. 1 to 3, the filter device 10 includes an expansion portion 20 which is a mesh-shaped tubular body, a distal side interlock portion 40 located on a distal side of the expansion portion 20, a proximal side interlock portion 50 located on a proximal side of the expansion portion 20, and an elongated shaft portion 30 interlocked with the proximal side interlock portion 50.

The shaft portion 30 is an elongated wire extending from an operator's hand-side to the proximal side interlock portion 50. Although the shaft portion 30 is flexible as shown in FIG. 1, the shaft portion 30 is sufficiently rigid to allow the operator to push the shaft portion 30 towards the distal side and transmit an axial force to the proximal side interlock portion 50 by way of the shaft portion 30. A distal side end portion of the shaft portion 30 is connected to the proximal side interlock portion 50. A material for forming the shaft portion 30 is not particularly limited. However, for example, stainless steel or a shape memory alloy can be preferably used.

The expansion portion 20 includes a plurality of elastically deformable linear bodies 21 (see FIG. 3). In the embodiments, the linear body 21 is a wire of one or more types. The linear body 21 is braided in a mesh shape to form a tubular body having a small diameter in both ends. The plurality of linear bodies 21 are braided to form a gap 21A between the linear bodies 21. The expansion portion 20 is interposed between the distal side interlock portion 40 and the proximal side interlock portion 50.

As illustrated in FIG. 3, the distal side interlock portion 40 includes an inner tube 41 located inside the linear body 21 and an outer tube 42 located outside the linear body 21. A distal portion of the linear body 21 is pinched and fixed between the inner tube 41 and the outer tube 42. An inner surface side of the inner tube 41 is a guide wire lumen 43 into which a guide wire can be inserted.

The proximal side interlock portion 50 includes an inner tube 51 located inside the linear body 21 and an outer tube 52 located outside the inner tube 51. A proximal portion of the linear body 21 and a distal portion of the shaft portion 30 are pinched and fixed between the inner tube 51 and the outer tube 52. Therefore, the proximal side interlock portion 50 is movable together with the shaft portion 30. An inner surface side of the inner tube 51 is a guide wire lumen 53 into which a guide wire can be inserted.

Figure 4:
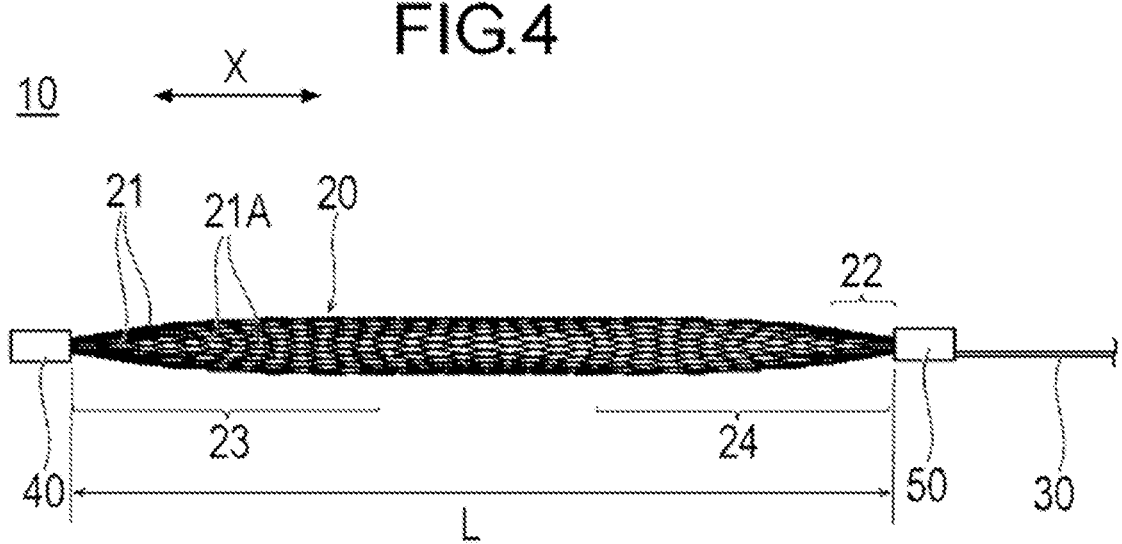
FIG. 4 is a plan view illustrating the expansion portion in a stretched state.

The expansion portion 20 is accommodated in a sheath (refer to FIG. 6A) until the expansion portion 20 is delivered to a desired position. In this manner, as illustrated in FIG. 4, the expansion portion 20 elastically deforms, and is brought into a stretched state where an outer diameter thereof decreases. In the stretched state, the expansion portion 20 is not turned back unlike the state shown in FIG. 2. When the expansion portion 20 is in the stretched state, the proximal side interlock portion 50 and the distal side interlock portion 40 are moved apart from each other along an axial direction X of the expansion portion 20. The expansion portion 20 includes a proximal gathering portion 22 which is a proximal portion of the expansion portion 20 in the stretched state. The proximal gathering portion 22 is located on the distal side of the proximal side interlock portion 50, and the plurality of linear bodies 21 are gathered therein.

As illustrated in FIGS. 1 to 3, in a natural state where the expansion portion 20 is released from the sheath 60 and no external force is applied thereto, the expansion portion 20 is brought into a turned-back state where the expansion portion 20 is turned back in the axial direction X while a diameter of the expansion portion 20 is enlarged due to a self-elastic force or restoring force of the linear body 21. In the turned-back state, the direction in which both side portions interposing a turned-back portion turned back in the axial direction X extend from the turned-back portion has a component facing the same direction along the axial direction X. The turned-back portion is orthogonal to the axial direction X. When the expansion portion 20 is in the turned-back state, the proximal side interlock portion 50 and the distal side interlock portion 40 which are located at both ends of the expansion portion 20 in the axial direction X move close to each other. A distance is changed between the proximal side interlock portion 50 and the distal side interlock portion 40. Accordingly, an outer diameter of the braided expansion portion 20 can be changed. The expansion portion 20 is accommodated again in the sheath 60. In this manner, the turned-back state is released, and the expansion portion 20 is brought into the stretched state again (refer to FIG. 7B).

As illustrated in FIGS. 3 and 4, the expansion portion 20 includes a distal portion 23 interlocked with the distal side interlock portion 40 and a proximal portion 24 interlocked with the proximal side interlock portion 50. In the turned-back state, as illustrated in FIG. 3, the proximal portion 24 enters the inside of the distal portion 23 having a cup shape open to the proximal side. That is, the expansion portion 20 is shaped in advance to have the cup shape. For example, the expansion portion 20 can be shaped by being accommodated inside a mold having a predetermined shape and heated.

As illustrated in FIGS. 3 and 5, the distal portion 23 has a maximum expansion portion 25 having the largest diameter in the natural state. In the natural state, the expansion portion 20 has a first turned-back portion 26 projecting in a proximal direction, a second turned-back portion 27 projecting in a distal direction, and a central portion 28 located between the first turned-back portion 26 and the second turned-back portion 27. The first turned-back portion 26 is located between the distal portion 23 and the second turned-back portion 27. The second turned-back portion 27 is located between the first turned-back portion 26 and the proximal portion 24. In a state where the expansion portion 20 is turned back, inner peripheral surfaces of the tubular expansion portion 20 are separated from each other without being in contact with each other. In the natural state, the expansion portion 20 has a three-layer structure by being turned back at two locations of the first turned-back portion 26 and the second turned-back portion 27. Respective layers of the three-layer structure are separated with a space therebetween.

As illustrated in FIG. 3, in the expansion portion 20, in the natural state, the proximal gathering portion 22 is located in the vicinity of a turned-back cross section P1 which is a cross section in which the first turned-back portion 26 is located, and which is a cross section orthogonal to the axial direction X. In this case, a radius of curvature of the second turned-back portion 27 is larger compared to a case where the proximal gathering portion 22 is located on the distal side from the vicinity of the turned-back cross section P1. In this manner, a diameter of the maximum expansion portion 25 increases, and a force received by the expansion portion 20 from a biological lumen wall increases. Therefore, in the filter device 10, a fixing force can be further improved inside the biological lumen. In alternative embodiments, the proximal gathering portion 22 is not located in the vicinity of the turned-back cross section P1.

In addition, in the natural state, the expansion portion 20 has three layers in a maximum portion cross section P2 which is a cross section in which the maximum expansion portion 25 is located, and which is a cross section orthogonal to the axial direction X. The expansion portion 20 need not have three layers in the maximum portion cross section P2. In alternative embodiments, the expansion portion 20 has the three layers at least in any cross section orthogonal to the axial direction X. In addition, the expansion portion 20 need not be turned back in the natural state.

The linear body 21 is formed of a Ni—Ti alloy which is a superelastic alloy or a shape memory alloy. Therefore, the expansion portion 20 has a highly elastic force. The linear body 21 is formed by plain weaving or twill weaving, and is braided in a tubular shape. The plain weaving is a weaving method of alternately raising and lowering warp yarns and weft yarns. The twill weaving is a weaving method of repeatedly causing the warp yarn to pass below one of the weft yarns after passing above a plurality of the weft yarns. Compared to the plain weaving, the twill weaving has fewer intersections where the warp yarn and the weft yarn are vertically interchanged with each other. In a case where the number of the linear bodies 21 is large, an intersection position of the linear bodies 21 formed by the twill weaving is unlikely to be shifted. The reason is as follows. In a case where the number of the linear bodies is large, when the warp yarn and the weft yarn are vertically less interchanged with each other, a shape of the linear body 21 is stabilized. In a case where the number of the linear bodies 21 is small, an intersection position of the linear bodies 21 formed by the plain weaving is unlikely to be shifted. The reason is as follows. In a case where the number of the linear bodies 21 is small, when the warp yarn and the weft yarn are vertically more interchanged with each other, the shape of the linear body 21 is stabilized.

A wire diameter d of the linear body 21 is not particularly limited, but is preferably 0.10 to 0.25 mm, more preferably 0.12 to 0.20 mm, and much more preferably 0.14 to 0.19 mm. Since the expansion portion 20 has the suitable wire diameter d, the expansion portion 20 can achieve a suitable fixing force inside the biological lumen. Furthermore, since the expansion portion 20 has the suitable wire diameter d, the expansion portion 20 can achieve suitable flexibility for being pulled and recovered into a pipe body such as the sheath 60 in a state where the expansion portion 20 indwells the biological lumen (refer to FIGS. 7A and 7B). When the wire diameter d of the linear body 21 is excessively large, the expansion portion 20 is unlikely to be turned back. Therefore, when a proximal portion of the expansion portion 20 is pushed in the distal direction to turn back the expansion portion 20, the expansion portion 20 is not turned back, and is likely to slip on the biological lumen wall. When the wire diameter d of the linear body 21 is excessively small, a contact force of the expansion portion 20 with respect to the biological lumen wall decreases. Therefore, when the proximal portion of the expansion portion 20 is pushed in the distal direction to turn back the expansion portion 20, the expansion portion 20 is likely to slip on the biological lumen wall.

It is preferable that the linear body 21 has two or more types of wires having different wire diameters d. In this manner, in a non-turned-back state, the proximal portion is pushed towards the distal direction. Accordingly, the linear body 21 which is thin and likely to be bent serves as a starting point, and the expansion portion 20 is likely to be brought into a turned-back state. The linear body 21 is braided around a central axis of the expansion portion 20 to be wound in two directions (i.e., the forward direction and reverse direction). Therefore, the expansion portion 20 has a plurality of linear bodies 21 wound in the forward direction and a plurality of linear bodies 21 wound in the reverse direction. Then, it is preferable that the plurality of linear bodies 21 wound in the forward direction have two or more types of wires having different wire diameters. Furthermore, it is preferable that the plurality of linear bodies 21 wound in the reverse direction have two or more types of wires having different wire diameters. The wire diameter of all of the linear bodies 21 wound in the forward direction may be identical. In addition, the wire diameter of all of the linear bodies 21 wound in the reverse direction may be identical.

The number of the linear bodies 21 is not particularly limited, but is preferably 16 to 48, more preferably 24 to 40, and much more preferably 30 to 36. When the number of the linear bodies 21 is large, the gap 21A formed in the expansion portion 20 decreases, and is likely to be clogged. When the number of the linear bodies 21 is small, a size of the gap 21A formed in the expansion portion 20 is likely to be uneven when the expansion portion 20 is turned back.

An outer diameter D of the maximum expansion portion 25 is not particularly limited, but is preferably 30 to 35 mm, and is more preferably 32 to 34 mm. In this manner, the expansion portion 20 can achieve both flexibility enabling easy turning back and an expansion force enabling fixing to biological lumens having different thicknesses. Therefore, the filter device 10 is applicable to various biological lumens having different diameters.

A length L of the expansion portion 20 in the axial direction X is preferably 80 to 110 mm, and is more preferably 90 to 100 mm in a stretched state where the expansion portion 20 is most stretched to separate both ends in the axial direction X. In this manner, a length of the expansion portion 20 in contact with the biological lumen wall can be suitably determined. Therefore, a fixing force of the expansion portion 20 to the biological lumen can be improved, and it is possible to suppress a possibility that the expansion portion 20 may be tilted or moved inside the biological lumen. When the expansion portion 20 is excessively short, the fixing force to the biological lumen is reduced, and the expansion portion 20 is likely to be tilted inside a thick biological lumen such as an inferior vena cava. When the expansion portion 20 is excessively long, the expansion portion 20 is likely to be moved by receiving the influence of body movements or the like.

A wire diameter of the linear body 21 is defined as d, and a sum of $d^3$ of all of the linear bodies 21 forming the expansion portion 20 is defined as S1. In this case, S1 is preferably 0.08 to 0.25 mm$^3$, and is more preferably 0.13 to 0.17 mm$^3$. In this manner, a force received from the biological lumen wall by the expansion portion 20 indwelling the biological lumen increases. For example, when the number of the linear bodies 21 having a wire diameter d1 is n1 and the number of the linear bodies 21 having a wire diameter d2 is n2, $S=n1\,(d1)^3+n2\,(d2)^3$ is satisfied. A section modulus of a wire having a circular cross section is $nd^3/32$, and is proportional to $d^3$. Accordingly, the sum of $d^3$ of all of the linear bodies 21 in the cross section can be an index indicating rigidity of the expansion portion 20.

Three times S1 is defined as S2. The expansion portion 20 has the three-layer structure. Accordingly, S2 which is three times S1 can be an index indicating the rigidity of the expansion portion 20 of the three-layer structure. For example, when the number of the linear bodies 21 having the wire diameter d1 is n1 and the number of the linear bodies 21 having the wire diameter d2 is n2, $S2=3S1=3\{n1(d1)^3+n2(d2)^3\}$ is satisfied. An area of a circumscribed circle C of the maximum expansion portion 25 in a maximum portion cross section P2 is defined as S3. A maximum outer diameter D of the linear body 21 in a natural state is a diameter of the circumscribed circle C. S3 is $nD^2/4$. When the area S3 of the circumscribed circle C is large, a cross-sectional area of the linear body 21 occupying S3 decreases, and the rigidity of the expansion portion 20 is likely to be weakened. S2/S3 is preferably $4\times10^{-4}$ to $10\times10^{-4}$ mm, and is more preferably $4\times10^{-4}$ to $7\times10^{-4}$ mm. In this manner, the expansion portion 20 fixed to the biological lumen wall can obtain suitable flexibility. Accordingly, a turned-back state where the expansion portion 20 is fixed to the biological lumen wall can be released when the shaft portion 30 is pulled. That is, the shaft portion 30 is pulled in the turned-back state of the expansion portion 20 indwelling the biological lumen. In this manner, while the expansion portion 20 is in a state of being suitably held on the biological lumen wall, the proximal portion 24 can be pulled out from the inside of distal portion 23 in the proximal direction. Therefore, it is easy to recover or retract the expansion portion 20 indwelling the biological lumen.

Next, a using method and an operation of the filter device 10 will be described.

Figure 6A:
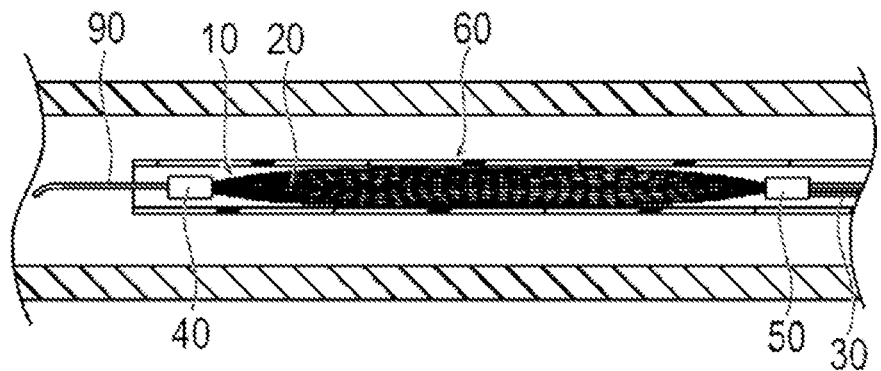
FIG. 6A is a cross-sectional view illustrates a state when the filter device is inserted into a blood vessel.

First, a guide wire 90 is inserted into a blood vessel. Next, a proximal side end portion of the guide wire 90 located outside the body is inserted into the guide wire lumens 43 and 53 (refer to FIG. 3) of the filter device 10. Subsequently, as illustrated in FIG. 6A, the filter device 10 is caused to reach a target position along the guide wire 90.

Figure 6B:
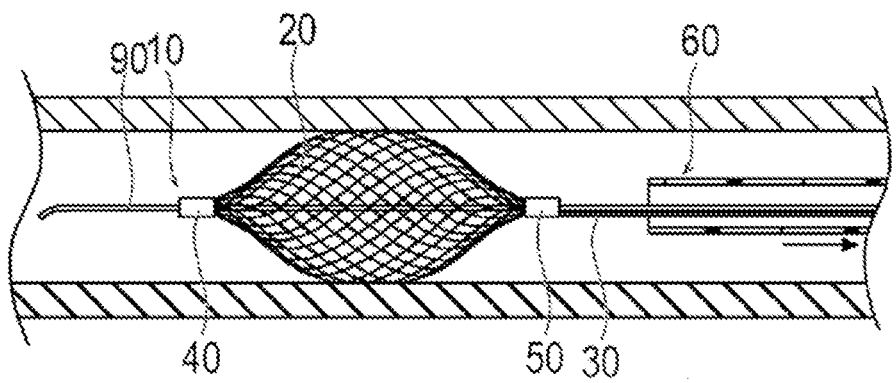
FIG. 6B is a cross-sectional view illustrating a state where the expansion portion is expanded inside the blood vessel.

Next, the sheath 60 is moved to the proximal side while the movement of the shaft portion 30 of the filter device 10 is restrained by hand. In this manner, the expansion portion 20 is released from the sheath 60 as illustrated in FIG. 6B. A pushing member (not illustrated) inserted into the sheath 60 may be used to push the expansion portion 20 from the sheath 60.

When the expansion portion 20 is released from the sheath 60, the proximal side interlock portion 50 and the distal side interlock portion 40 move closer to each other. Then, the expansion portion 20 expands due to a self-restoring force, and comes into contact with a vascular inner wall surface. At this time, the expansion portion 20 is in a stretched state where the expansion portion 20 is not turned back. The expansion portion 20 may be brought into a turned-back state by being released from the sheath 60.

Figure 6C:
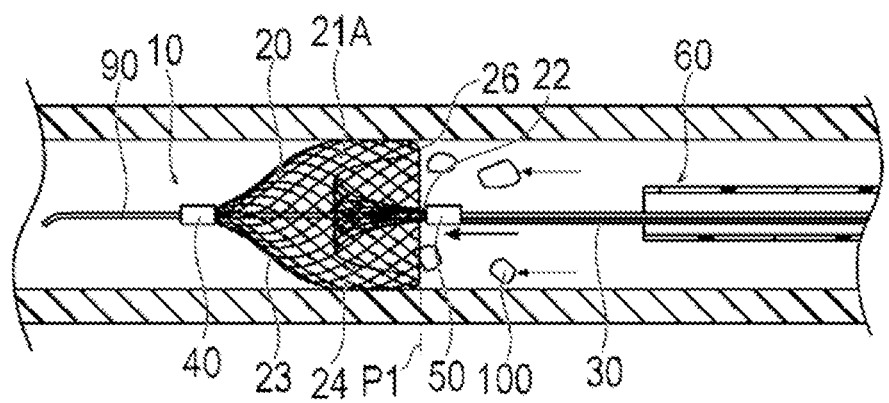
FIG. 6C is a cross-sectional view illustrating a state where the expansion portion is turned back.

Next, the shaft portion 30 is moved towards the distal side, and the proximal side interlock portion 50 is pushed into the distal side. In this manner, as illustrated in FIG. 6C, the expansion portion 20 is brought into a turned-back state of being turned back in the first turned-back portion 26. The sheath 60 may be moved towards the distal direction instead of the shaft portion 30. In this manner, the sheath 60 may push the proximal portion of the expansion portion 20 to turn back the expansion portion 20. The expansion portion 20 is formed in a mesh shape. Accordingly, the expansion portion 20 bites into the vascular inner wall surface, and is firmly fixed thereto. A maximum diameter of the expansion portion 20 in a natural state is larger than the diameter of the blood vessel to which the expansion portion 20 is inserted. Therefore, the expansion portion 20 is brought into a state where the expansion portion 20 is not completely expanded inside the blood vessel, and an expansion force is generated so that the expansion portion 20 is effectively fixed to a vascular wall. The proximal gathering portion 22 of the expansion portion 20 is located in the vicinity of the turned-back cross section P1 where the first turned-back portion 26 is located. Thereafter, the guide wire 90 is removed. In some embodiments, the guide wire 90 is not removed.

Next, for example, on an upstream side of the expansion portion 20, an object such as a plaque or a calcified lesion attached to the blood vessel of the inferior vena cava or the like is broken. A broken object 100 reaches the expansion portion 20, located on a downstream side. Blood can pass through the expansion portion 20 through the gap 21A. Then, the object 100 reaching the expansion portion 20 together with the blood is collected in the expansion portion 20. The expansion portion 20 has a recessed shape in which the proximal side which is the upstream side of a blood flow is open. Accordingly, the object 100 can be effectively collected.

As illustrated in FIGS. 3, 5, and 6C, in a turned-back state, the expansion portion 20 is a state where the inner surfaces are separated from each other without being in contact with each other. Therefore, a space is formed between respective layers of the three-layer structure. Therefore, the gap 21A functioning as a filter of the expansion portion 20 can be satisfactorily maintained. Therefore, the blood flowing through the gap 21A of the expansion portion 20 can be suitably maintained, and burden on a living body can be reduced. In addition, the inner surfaces of the expansion portion 20 do not come into contact with each other. Accordingly, a range functioning as the filter of the expansion portion 20 can be widely secured.

Next, the object 100 collected in the expansion portion 20 is removed. For example, the object 100 collected in the expansion portion 20 is aspirated and removed by the sheath 60 provided with an aspiration force from the proximal side. A method of removing the object 100 collected in the expansion portion 20 is not limited.

Figure 7A:
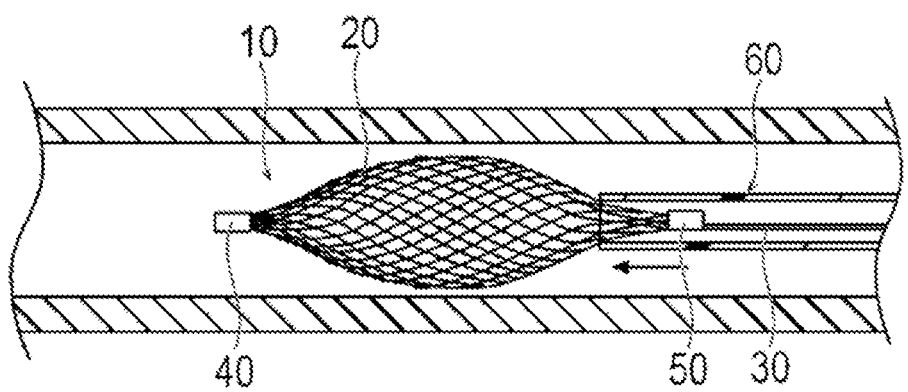
FIG. 7A is a cross-sectional view illustrating a state where a proximal portion of the expansion portion is recovered to a sheath.

After the object 100 such as a thrombus is completely aspirated by the sheath 60, as illustrated in FIG. 7A, the sheath 60 is pushed towards the distal direction while the movement of the shaft portion 30 is restrained by hand. At this time, the shaft portion 30 may be pulled towards the proximal side. In this manner, while the proximal side interlock portion 50 enters the inside of the sheath 60, the proximal side interlock portion 50 is separated from the distal side interlock portion 40. Then, the expansion portion 20 is brought into a stretched state from a turned-back state, and is accommodated inside the sheath 60 from the proximal side.

Figure 7B:
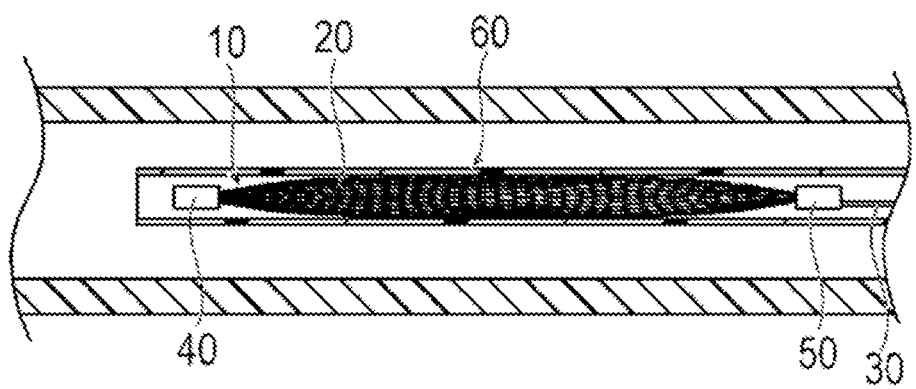
FIG. 7B is a cross-sectional view illustrating a state where the whole expansion portion is recovered to the sheath.

As illustrated in FIG. 7B, after the expansion portion 20 is accommodated inside the sheath 60, the filter device 10 is removed from the blood vessel together with the sheath 60, thereby completing the procedure.

As described above, in the filter device 10, the filter device 10 inserted into the biological lumen to collect the object includes the elongated shaft portion 30, and the elastically deformable tubular expansion portion 20 interlocked with the shaft portion 30, and braided with the plurality of linear bodies 21 formed of a Ni—Ti alloy to include the gap 21A. In a case where the wire diameter of the linear body 21 is defined as d and the sum of $d^3$ of all of the linear bodies 21 is defined as S1, S1 is 0.08 to 0.25 $mm^3$.

In the filter device 10 configured as described above, a force received from the biological lumen wall by the expansion portion 20 indwelling the biological lumen increases. Therefore, the filter device 10 can improve the fixing force inside the biological lumen. In a natural state, the expansion portion 20 may be turned back or may not be turned back in the axial direction. For example, in the expansion portion 20, in a cross section which is parallel to an axis and where the axis is located, a distal portion of the expansion portion 20 projecting outward in a radial direction and a proximal portion of the expansion portion 20 projecting inward in the radial direction may be interlocked with each other at a tangent line perpendicular to the axis. A portion from the first turned-back portion to the second turned-back portion 27 may be located outside the distal portion 23.

The expansion portion 20 has the distal portion 23, the proximal portion 24, the first turned-back portion 26 turned back in the axial direction X between the distal portion 23 and the proximal portion 24 and projecting towards the proximal direction, and the second turned-back portion 27 turned back in the axial direction X between the first turned-back portion 26 and the proximal portion 24 and projecting towards the distal direction. In this manner, the expansion force of the expansion portion 20 is increased by being turned back, and the force received from the biological lumen wall by the expansion portion 20 increases. Therefore, the filter device 10 can improve the fixing force inside the biological lumen.

The expansion portion 20 has the proximal gathering portion 22 in which the plurality of linear bodies 21 gather in the proximal portion, and the proximal gathering portion 22 is located in the vicinity of the maximum portion cross section P2 orthogonal to the axial direction X in which the first turned-back portion 26 is located. In this manner, the expansion force of the expansion portion 20 increases, and the force received from the biological lumen wall by the expansion portion 20 increases. Therefore, the filter device 10 can improve the fixing force inside the biological lumen.

The expansion portion 20 has three layers in the maximum portion cross section P2 orthogonal to the axial direction X in which the maximum expansion portion 25 having the largest diameter is located. In this manner, the expansion portion 20 has the three layers at a position of the maximum expansion portion 25 which is likely to come into contact with the biological lumen wall. Accordingly, the expansion force increases, and the force received from the biological lumen wall by the expansion portion 20 increases. Therefore, the filter device 10 can improve the fixing force inside the biological lumen.

When three times S1 is defined as S2 and the area of the circumscribed circle C of the maximum expansion portion 25 in a cross section orthogonal to the axial direction X in which the maximum expansion portion 25 is located is defined as S3, it is preferable that S2/S3 is $4 \times 10^{-4}$ to $10 \times 10^{-4}$ mm. In this manner, the expansion portion 20 fixed to the biological lumen wall obtains suitable flexibility. Accordingly, when the shaft portion 30 is pulled, a turned-back state of the expansion portion 20 which is fixed to the biological lumen wall can be satisfactorily released. That is, the shaft portion 30 is pulled in the turned-back state of the expansion portion 20 indwelling the biological lumen. In this manner, while the expansion portion 20 is in a state of being suitably held in the biological lumen wall, and the proximal portion 24 can be pulled out from the inside of the distal portion 23 in the proximal direction. Therefore, it is easy to recover the expansion portion 20 indwelling the biological lumen.

It is preferable that the expansion portion 20 is formed by plain weaving or twill weaving. In this manner, the expansion portion 20 can maintain a suitable shape since an intersection position of the intersecting linear bodies 21 is unlikely to be shifted. When the number of the linear bodies 21 is large, the intersection position of the linear bodies 21 formed by the twill weaving is unlikely to be shifted. When the number of the linear bodies 21 is small, the intersection position of the linear bodies 21 formed by the plain weaving is unlikely to be shifted. The expansion portion 20 can maintain a suitable fixing force since the intersection position is unlikely to be shifted.

The outer diameter of the maximum expansion portion 25 having the largest diameter of the expansion portion 20 is preferably 30 to 35 mm. In this manner, the expansion portion 20 can achieve both flexibility enabling easy turning back and the expansion force enabling fixing to biological lumens having different diameters. Therefore, the filter device 10 is applicable to various biological lumens having different diameters.

The wire diameter d of the linear body 21 is preferably 0.10 to 0.25 mm. In this manner, since the expansion portion 20 has the suitable wire diameter d, the expansion portion 20 achieves a suitable fixing force inside the biological lumen. Furthermore, since the expansion portion 20 has the suitable wire diameter d, the expansion portion 20 can achieve suitable flexibility for being pulled into a pipe body such as the sheath 60 and recovered in a state where the expansion portion indwells the biological lumen. The outer diameter of the pipe body such as the sheath 60 which recovers the linear body 21 is 7 Fr to 9 Fr, and preferably 8 Fr. Here, 1 Fr is approximately 0.33 mm.

It is preferable that the linear body 21 has two or more types of wires having different wire diameters d. In this manner, the proximal portion is pushed towards the distal direction inside the biological lumen. Accordingly, the linear body 21 which is thin and likely to be bent serves as a starting point, and the expansion portion 20 is likely to be brought into a turned-back state.

The number of the linear bodies 21 is preferably 16 to 48. When the number of the linear bodies 21 is large, the gap 21A formed in the expansion portion 20 is likely to be clogged. When the number of the linear bodies 21 is small, a size of the gap 21A formed in the expansion portion 20 is likely to be uneven when the expansion portion 20 is turned back.

The length of the expansion portion 20 in the axial direction X is preferably 80 to 110 mm in a stretched state where the expansion portion 20 is most stretched to separate both ends in the axial direction X. In this manner, the length of the expansion portion 20 in contact with the biological lumen wall can be suitably determined. Therefore, the fixing force of the expansion portion 20 to the biological lumen can be improved, and it is possible to suppress a possibility that the expansion portion 20 may be tilted or moved inside the biological lumen. When the expansion portion 20 is excessively short, the fixing force to the biological lumen is reduced, and the expansion portion 20 is likely to be tilted inside the biological lumen. When the expansion portion 20 is excessively long, the expansion portion 20 is likely to be moved by receiving the influence of body movements or the like.

In addition to the above-described embodiments, various modifications can be made by those skilled in the art within the technical idea of the present invention. For example, the shaft portion 30 may be interlocked with the distal side interlock portion 40 instead of the proximal side interlock portion 50. The shaft portion 30 may be interlocked with the proximal side interlock portion 50 or the distal side interlock portion 40 to be relatively rotatable or movable. In addition, the guide wire lumens 53 and 43 may not be formed in the proximal side interlock portion 50 and the distal side interlock portion 40.

EXAMPLES

Hereinafter, evaluation results of some specific examples of the filter device 10 and comparative examples will be described. The structure and configuration of the filter device 10 are not limited to those examples.

1. <Evaluation of S1>

Filter devices 10 of Examples 1 to 4 and Comparative Examples 1 to 3 below were prepared to perform a test for evaluating an effect of S1 (sum of $d^3$ of all of the linear bodies 21) on fixing ability of the expansion portion 20 to the blood vessel, and an effect of S1 on recovering ability to the sheath 60.

Example 1

16 linear bodies 21 having a wire diameter d=0.12 mm and 16 linear bodies 21 having a wire diameter d=0.15 mm were prepared. Next, the linear bodies 21 were braided by the plain weaving to form the expansion portion 20, and the filter device 10 of Example 1 was prepared. A material for the linear body 21 was a Ni—Ti alloy manufactured by Daido Steel Co., Ltd. During the braiding, the linear bodies 21 having different wire diameters were alternately disposed in each of a group of the linear bodies 21 aligned in the forward direction and a group of the linear bodies 21 aligned in the reverse direction. In a natural state, the extension portion 20 was shaped so that the expansion portion 20 is brought into a turned-back state. The length L of the prepared expansion portion 20 in the axial direction was 95 mm in a state where the expansion portion 20 was most stretched in the axial direction (i.e., the state where the distal side interlock portion 40 and the proximal side interlock portion 50 were most separated from each other). S1 (i.e., the sum of $d^3$ of all of the linear bodies 21) was 0.08 mm$^3$.

Example 2

16 linear bodies 21 having a wire diameter d=0.14 mm and 16 linear bodies 21 having a wire diameter d=0.18 mm were prepared. The other conditions of the expansion portion 20 of Example 2 were similar to Example 1. S1 was 0.14 mm$^3$.

Example 3

24 linear bodies 21 having a wire diameter d=0.12 mm and 24 linear bodies 21 having a wire diameter d=0.20 mm were prepared. The other conditions of the expansion portion 20 of Example 3 were similar to Example 1. S1 was 0.23 mm$^3$.

Example 4

24 linear bodies 21 having a wire diameter d=0.13 mm and 24 linear bodies 21 having a wire diameter d=0.20 mm were prepared. The other conditions of the expansion portion 20 of Example 4 were similar to Example 1. S1 was 0.25 mm$^3$.

Comparative Example 1

72 linear bodies having a wire diameter d=0.10 mm were prepared. Next, the linear bodies were braided by the plain weaving to form the expansion portion for the filter device of Comparative Example 1. The material for the linear body was the Ni—Ti alloy manufactured by Daido Steel Co., Ltd. In a natural state, the extension portion was shaped so that the expansion portion is brought into a turned-back state. The length L of the prepared expansion portion in the axial direction was 95 mm in a state where the expansion portion was most stretched in the axial direction (i.e., the state where the distal side interlock portion and the proximal side interlock portion were most separated from each other). S1 was 0.07 mm$^3$.

Comparative Example 2

32 linear bodies having a wire diameter d=0.20 mm were prepared. The other conditions of the expansion portion of Comparative Example 2 were similar to Comparative Example 1. S1 was 0.26 mm$^3$.

Comparative Example 3

72 linear bodies having a wire diameter d=0.16 mm were prepared. The other conditions of the expansion portion of Comparative Example 3 were similar to Comparative Example 1. S1 was 0.29 mm$^3$.

(Effect Evaluation Test of S1 on Fixing Ability and Recovering Ability)

The expansion portions 20 of the filter devices 10 of Examples 1 to 4 and those of Comparative Examples 1 to 3 were accommodated in the sheath 60, and were expanded after being released from the sheath 60 inside a simulated blood vessel, which is an excised porcine blood vessel having an inner diameter being approximately 26 mm. Each expansion portion 20 came into contact with a vascular inner wall without being turned back. Thereafter, the shaft portion 30 was pushed towards the distal direction, and the fixing ability of the expansion portion 20 to the vascular inner wall surface was evaluated based on whether or not the expansion portion 20 was turned back. Specifically, when the expansion portion 20 is in a turned-back state, the fixing ability was determined to be suitable, and when the expansion portion 20 is not in the turned-back state, the fixing ability was determined to be unsuitable.

Furthermore, after the expansion portion 20 indwells the simulated blood vessel, the sheath 60 and the shaft portion 30 were operated to attempt to recover the expansion portion 20 into the sheath 60 while the expansion portion 20 is contracted. In a case where a maximum load was lower than 500 gf when the expansion portion 20 was recovered into the sheath 60 at a speed of 1 mm/s, it was determined that recovery resistance was small and recovering ability was suitable. In a case where the maximum load was 500 gf or higher, it was determined that the recovery resistance was great and the recovering ability was unsuitable. The load was measured by using a digital force gauge. Results are illustrated in Table 1.

TABLE 1

| | Wire Diameter d | Number of Linear Bodies | Length L | S1 | Fixing Ability | Recovering ability |
|---|---|---|---|---|---|---|
| Comparative Example 1 | 0.10 mm | 72 | 95 mm | 0.07 mm$^3$ | x | ○ |
| Example 1 | 0.12 mm<br>0.15 mm | 16<br>16 | 95 mm | 0.08 mm$^3$ | ○ | ○ |
| Example 2 | 0.14 mm<br>0.18 mm | 16<br>16 | 95 mm | 0.14 mm$^3$ | ○ | ○ |
| Example 3 | 0.12 mm<br>0.20 mm | 24<br>24 | 95 mm | 0.23 mm$^3$ | ○ | ○ |
| Example 4 | 0.13 mm<br>0.20 mm | 24<br>24 | 95 mm | 0.25 mm$^3$ | ○ | ○ |
| Comparative Example 2 | 0.20 mm | 32 | 95 mm | 0.26 mm$^3$ | ○ | x |
| Comparative Example 3 | 0.16 mm | 72 | 95 mm | 0.29 mm$^3$ | ○ | x |

(Result of Effect Evaluation Test of S1 on Fixing Ability)

In Comparative Example 1, the expansion portion slipped on the inner wall surface of the simulated blood vessel due to an insufficient fixing force to the simulated blood vessel, and was not turned back. Therefore, the fixing ability of Comparative Example 1 was unsuitable. In contrast, in Examples 1 to 4 and Comparative Examples 2 and 3, the expansion portion 20 had a strong fixing force to the simulated blood vessel, and was turned back without slipping on the inner wall surface of the simulated blood vessel. Therefore, the fixing ability of Examples 1 to 4 and Comparative Examples 2 and 3 was suitable.

(Result of Effect Evaluation Test of S1 on Recovering Ability)

In Comparative Examples 2 and 3, the recovery resistance for recovering the expansion portion to the sheath was 500 kgf or higher. Therefore, the recovering ability of Comparative Examples 2 and 3 was unsuitable. In contrast, in Examples 1 to 4 and Comparative Example 1, the recovery resistance of the expansion portion 20 was lower than 500 kgf. Therefore, the recovering ability of Examples 1 to 4 and Comparative Example 1 was suitable.

2. <Evaluation of S2/S3>

Filter devices 10 of Examples 5 to 8 and Comparative Examples 4 and 5 below were prepared to perform a test for evaluating an effect of S2/S3 on the fixing ability of the expansion portion 20 to the blood vessel, and an effect of S2/S3 on the recovering ability of the sheath 60.

Example 5

16 linear bodies 21 having the wire diameter d=0.14 mm and 16 linear bodies 21 having the wire diameter d=0.18 mm were prepared. The maximum outer diameter D of the expansion portion 20 was set to 35 mm. The other conditions were the same as those in Example 1. S2/S3 was $4 \times 10^{-4}$ mm.

Example 6

The linear bodies 21 same as Example 5 were used. The maximum outer diameter D of the expansion portion 20 was set to 32 mm, and the other conditions were the same as those in Example 5. S2/S3 was $5 \times 10^{-4}$ mm.

Example 7

16 linear bodies 21 having the wire diameter d=0.16 mm and 16 linear bodies 21 having the wire diameter d=0.20 mm were prepared. The maximum outer diameter D of the expansion portion 20 was set to 35 mm. The other conditions were the same as those in Example 5. S2/S3 was $6 \times 10^{-4}$ mm.

Example 8

24 linear bodies 21 having the wire diameter d=0.12 mm and 24 linear bodies 21 having the wire diameter d=0.20 mm were prepared. The maximum outer diameter D of the expansion portion 20 was set to 30 mm. The other conditions were the same as those in Example 5. S2/S3 was $10 \times 10^{-4}$ mm.

Comparative Example 4

72 linear bodies having the wire diameter d=0.10 mm were prepared. The maximum outer diameter D of the expansion portion was set to 30 mm. The other conditions were the same as those in Example 5. S2/S3 was $3 \times 10^{-4}$ mm.

Comparative Example 5

24 linear bodies having the wire diameter d=0.14 mm and 24 linear bodies having the wire diameter d=0.20 mm were prepared. The maximum outer diameter D of the expansion portion was set to 30 mm. The other conditions were the same as those in Example 5. S2/S3 was $11 \times 10^{-4}$ mm.

(Effect Evaluation Test of S2/S3 on Fixing Ability and Recovering Ability)

The filter devices 10 of Examples 5 to 8 and those of Comparative Examples 4 and 5 were used to perform an effect evaluation test on the fixing ability and the recovering ability of the expansion portion 20 by using a method the same as that of [the effect evaluation test of S1 on the fixing ability and the recovering ability] described above. Results are illustrated in Table 2.

TABLE 2

| | Wire Diameter d | Number of Linear Bodies | Maximum Outer Diameter D | S1 | S2/S3 | Fixing Ability | Recovering ability |
|---|---|---|---|---|---|---|---|
| Comparative Example 4 | 0.10 mm | 72 | 30 mm | 0.07 mm$^3$ | $3 \cdot 10^{-4}$ mm | x | ○ |
| Example 5 | 0.14 mm<br>0.18 mm | 16<br>16 | 35 mm | 0.14 mm$^3$ | $4 \cdot 10^{-4}$ mm | ○ | ○ |
| Example 6 | 0.14 mm<br>0.18 mm | 16<br>16 | 32 mm | 0.14 mm$^3$ | $5 \cdot 10^{-4}$ mm | ○ | ○ |
| Example 7 | 0.16 mm<br>0.20 mm | 16<br>16 | 35 mm | 0.19 mm$^3$ | $6 \cdot 10^{-4}$ mm | ○ | ○ |
| Example 8 | 0.12 mm<br>0.20 mm | 24<br>24 | 30 mm | 0.23 mm$^3$ | $10 \cdot 10^{-4}$ mm | ○ | ○ |
| Comparative Example 5 | 0.14 mm<br>0.20 mm | 24<br>24 | 30 mm | 0.26 mm$^3$ | $11 \cdot 10^{-4}$ mm | ○ | x |

(Result of Effect Evaluation Test of S2/S3 on Fixing Ability)

In Comparative Example 4, the expansion portion slipped on the inner wall surface of the simulated blood vessel due to the insufficient fixing force to the simulated blood vessel, and was not turned back. Therefore, the fixing ability of Comparative Example 4 was unsuitable. In contrast, in Examples 5 to 8 and Comparative Example 5, the expansion portion 20 had the strong fixing force to the simulated blood vessel, and was turned back without slipping on the inner wall surface of the simulated blood vessel. Therefore, the fixing ability of Examples 5 to 8 and Comparative Example 5 was suitable.

(Effect Evaluation Test of S2/S3 on Recovering Ability)

In Comparative Example 5, the recovery resistance for recovering the expansion portion to the sheath was 500 kgf or higher. Therefore, the recovering ability of Comparative Example 5 was unsuitable. In contrast, in Examples 5 to 8 and Comparative Example 4, the recovery resistance of the expansion portion 20 was lower than 500 kgf. Therefore, the recovering ability of Examples 5 to 8 and Comparative Example 4 was suitable.

3. <Evaluation of Maximum Outer Diameter of Expansion Portion>

Filter devices 10 of Examples 9 to 13 below were prepared to perform a test for evaluating an effect of the maximum outer diameter D of the expansion portion 20 in a natural state on the fixing ability of the expansion portion 20 to the blood vessel, and an effect of the maximum outer diameter D on the recovering ability of the sheath 60.

Example 9

16 linear bodies 21 having the wire diameter d=0.14 mm and 16 linear bodies 21 having the wire diameter d=0.18 mm were prepared. The maximum outer diameter of the expansion portion 20 was set to 29 mm. The other conditions were the same as those in Example 1.

Example 10

The maximum outer diameter of the expansion portion 20 was set to 30 mm. The other conditions were the same as those in Example 9.

Example 11

The maximum outer diameter of the expansion portion 20 was set to 33 mm. The other conditions were the same as those in Example 9.

Example 12

The maximum outer diameter of the expansion portion 20 was set to 35 mm. The other conditions were the same as those in Example 9.

Example 13

The maximum outer diameter of the expansion portion 20 was set to 36 mm. The other conditions were the same as those in Example 9.

(Effect Evaluation Test of Maximum Outer Diameter of Expansion Portion on Fixing Ability and Recovering Ability)

The filter devices 10 of Examples 9 to 13 were used to perform an effect evaluation test on the fixing ability and the recovering ability of the expansion portion 20 by using a method the same as that of [the effect evaluation test of S1 on the fixing ability and the recovering ability] described above. Results are illustrated in Table 3.

TABLE 3

|  | Wire Diameter d | Number of Linear Bodies | Length L | Maximum Outer Diameter D | S1 | Fixing Ability | Recovering ability |
|---|---|---|---|---|---|---|---|
| Example 9 | 0.14 mm<br>0.18 mm | 16<br>16 | 95 mm | 29 mm | 0.14 mm$^3$ | Δ | ○ |
| Example 10 | 0.14 mm<br>0.18 mm | 16<br>16 | 95 mm | 30 mm | 0.14 mm$^3$ | ○ | ○ |
| Example 11 | 0.14 mm<br>0.18 mm | 16<br>16 | 95 mm | 33 mm | 0.14 mm$^3$ | ○ | ○ |
| Example 12 | 0.14 mm<br>0.18 mm | 16<br>16 | 95 mm | 35 mm | 0.14 mm$^3$ | ○ | ○ |
| Example 13 | 0.14 mm<br>0.18 mm | 16<br>16 | 95 mm | 36 mm | 0.14 mm$^3$ | ○ | Δ |

(Result of Effect Evaluation Test of Maximum Outer Diameter of Expansion Portion on Fixing Ability)

In Example 9, the expansion portion 20 slipped on the inner wall surface of the simulated blood vessel due to the insufficient fixing force to the simulated blood vessel, and was not turned back. Therefore, the fixing ability of Example 9 was unsuitable. In contrast, in Examples 10 to 13, the expansion portion 20 had the strong fixing force to the simulated blood vessel, and was turned back without slipping on the inner wall surface of the simulated blood vessel. Therefore, the fixing ability of Examples 10 to 13 was suitable.

(Result of Effect Evaluation Test of Maximum Outer Diameter of Expansion Portion on Recovering Ability)

In Example 13, the recovery resistance for recovering the expansion portion 20 to the sheath 60 was 500 kgf or higher. Therefore, the recovering ability of Example 13 was unsuitable. In contrast, in Examples 9 to 12, the recovery resistance of the expansion portion 20 was lower than 500 kgf. Therefore, the recovering ability of Examples 9 to 12 was suitable.

4. <Evaluation of Length of Expansion Portion>

Filter devices 10 of Examples 14 to 19 below were prepared to perform a test for evaluating an effect of the length L in the axial direction of the expansion portion 20 most stretched in the axial direction on tilting stability of the expansion portion 20 to the blood vessel, and an effect of the length L on operability.

Example 14

16 linear bodies 21 having the wire diameter d=0.14 mm and 16 linear bodies 21 having the wire diameter d=0.18 mm were prepared. The maximum outer diameter of the expansion portion 20 was set to 34 mm, and the length L of the expansion portion 20 was set to 75 mm. The other conditions were the same as those in Example 1.

Example 15

The length L of the expansion portion 20 was set to 80 mm. The other conditions were the same as those in Example 14.

Example 16

The length L of the expansion portion 20 was set to 90 mm. The other conditions were the same as those in Example 14.

Example 17

The length L of the expansion portion 20 was set to 100 mm. The other conditions were the same as those in Example 14.

Example 18

The length L of the expansion portion 20 was set to 110 mm. The other conditions were the same as those in Example 14.

Example 19

The length L of the expansion portion 20 was set to 115 mm. The other conditions were the same as those in Example 14.

(Effect Evaluation Test of Length of Expansion Portion on Tilting Stability and Operability)

The expansion portions 20 of the filter devices 10 of Examples 14 to 19 were accommodated in the sheath 60, and were expanded after being released from the sheath 60 inside the simulated blood vessel, which is an excised porcine blood vessel having an inner diameter being approximately 26 mm. Each expansion portion 20 came into contact with the vascular inner wall without being turned back. Thereafter, the shaft portion 30 was pushed towards the distal direction, and the expansion portion 20 was brought into a turned-back state. Tilting stability of the expansion portion 20 with respect to the vascular inner wall surface was evaluated, based on whether or not the turned-back expansion portion 20 indwelling the blood vessel was tilted with respect to the blood vessel. Specifically, when the expansion portion 20 was tilted with respect to the vascular inner wall surface, the tilting stability was determined to be unsuitable. When not tilted, the tilting stability was determined to be suitable. In addition, a series of operability was determined until the expansion portion 20 of the filter device 10 was recovered to the sheath 60 after indwelling the simulated blood vessel and being brought into a turned-back state. Results are illustrated in Table 4.

TABLE 4

|  | Wire Diameter d | Number of Linear Bodies | Maximum Outer Diameter D | Length L | S1 | Tilting Stability | Operability |
|---|---|---|---|---|---|---|---|
| Example 14 | 0.14 mm 0.18 mm | 16 16 | 34 mm | 75 mm | 0.14 mm$^3$ | Δ | ○ |
| Example 15 | 0.14 mm 0.18 mm | 16 16 | 34 mm | 80 mm | 0.14 mm$^3$ | ○ | ○ |
| Example 16 | 0.14 mm 0.18 mm | 16 16 | 34 mm | 90 mm | 0.14 mm$^3$ | ○ | ○ |
| Example 17 | 0.14 mm 0.18 mm | 16 16 | 34 mm | 100 mm | 0.14 mm$^3$ | ○ | ○ |
| Example 18 | 0.14 mm 0.18 mm | 16 16 | 34 mm | 110 mm | 0.14 mm$^3$ | ○ | ○ |
| Example 19 | 0.14 mm 0.18 mm | 16 16 | 34 mm | 115 mm | 0.14 mm$^3$ | ○ | Δ |

(Effect Evaluation Test of Length of Expansion Portion on Tilting Stability)

In Example 14, the expansion portion 20 was short in the axial direction. Accordingly, the expansion portion 20 was tilted with respect to the simulated blood vessel. Therefore, the tilting stability of Example 14 was unsuitable. In contrast, in Examples 15 to 19, the expansion portion 20 was long in the axial direction. Accordingly, the expansion portion 20 was not tilted with respect to the simulated blood vessel. Therefore, the tilting stability of Examples 15 to 19 was suitable.

(Effect Evaluation Test of Length of Expansion Portion on Operability)

In Example 19, the expansion portion 20 was excessively long. Accordingly, the operability was unsuitable. In contrast, in Examples 14 to 18, the expansion portion 20 was not excessively long. Accordingly, the operability was suitable.

What is claimed is:

1. A filter device insertable into a biological lumen, comprising:
a shaft portion; and
an elastically deformable portion having a plurality of wires braided in a mesh shape, the deformable portion being connected to a first member at a first end of the deformable portion and a second member at a second end of the deformable portion, the first member being located at a distal end of the filter device, wherein
the second member includes an inner tube and an outer tube surrounding the inner tube, and a distal end of the shaft portion is between the inner and outer tubes of the second member, and
the wires include wires of a first type, each having a diameter d, and a sum of d$^3$ of all of the wires is 0.08 to 0.25 mm$^3$.

2. The filter device according to claim 1, wherein the wires are formed of a Ni—Ti alloy.

3. The filter device according to claim 1, wherein the deformable portion has a tubular shape when both ends thereof are stretched along an axial direction.

4. The filter device according to claim 3, wherein a length of the deformable portion along the axial direction is 80 to 110 mm when said both ends are stretched.

5. The filter device according to claim 1, wherein the deformable portion includes:
a distal portion,
a proximal portion located closer to the shaft portion than the distal portion,
a first turned-back portion located between the distal and proximal portions and protruding in a first direction from the distal portion to the proximal portion, and
a second turned-back portion located between the first turned-back portion and the proximal portion and protruding in a second direction opposite to the first direction.

6. The filter device according to claim 5, wherein
the proximal portion includes a proximal gathering portion, and
the proximal gathering portion and the first turned-back portion are located on a same plane that is orthogonal to the first direction.

7. The filter device according to claim 5, wherein the distal portion includes a maximum expansion portion of the filter device at which a distance from a line between the distal and proximal portions along a third direction orthogonal to the first direction, is largest.

8. The filter device according to claim 7, wherein the wires form three layers on a plane that is orthogonal to the first direction and on which the maximum expansion portion is located.

9. The filter device according to claim 8, wherein (3×S1)/S3, where S1 is 0.08 to 0.25 mm$^3$ and S3 is an area of a circumscribed circle formed by the maximum expansion portion on the plane, is 4×10$^{-4}$ to 10×10$^{-4}$ mm.

10. The filter device according to claim 7, wherein the distance is 30 to 35 mm.

11. The filter device according to claim 5, wherein a proximal end of the proximal portion of the deformable portion is between the inner and outer tubes of the second member.

12. The filter device according to claim 1, wherein the deformable portion is formed by plain weaving or twill weaving.

13. The filter device according to claim 1, wherein the diameter d is 0.10 to 0.25 mm.

14. The filter device according to claim 1, wherein the wires include wires of a second type having a diameter that is different from d.

15. The filter device according to claim 1, wherein a total number of the wires is 16 to 48.

16. A medical device for filtering an object in a body lumen, comprising:
- a mesh filter formed of a plurality of wires and connected to a first member at a first end of the filter and a second member at a second end of the filter, the first member located at a distal end of the medical device; and
- a shaft connected to the second member, wherein
- the second member includes an inner tube and an outer tube surrounding the inner tube, and a distal end of the shaft is between the inner and outer tubes of the second member,
- the mesh filter is deformable and has a natural state in which the wires are bent between the first and second members and expanded radially and a stretched state in which the wires are stretched, and
- the first and second members are separated by a first distance when the mesh filter is in the natural state and are separated by a second distance greater than the first distance when the mesh filter is in the stretched state.

17. The medical device according to claim 16, wherein in the natural state the wires are bent towards a first direction from the first member to the second member and further bent towards a second direction opposite to the first direction.

18. The medical device according to claim 16, wherein the mesh filter is symmetrical about a center axis that extends between the first and second members, and a maximum diameter of the mesh filter in the natural state is greater than a maximum diameter of mesh filter in the stretched state.

19. The medical device according to claim 16, wherein a proximal end of the mesh filter is between the inner and outer tubes of the second member.

* * * * *